(12) United States Patent
Pasquino et al.

(10) Patent No.: US 11,583,395 B2
(45) Date of Patent: Feb. 21, 2023

(54) PROSTHETIC HEART VALVE LEAFLET WITH VARIABLE THICKNESS

(71) Applicant: Epygon, Paris (FR)

(72) Inventors: Enrico Pasquino, Savigny (CH); Marcio Scorsin, Luxembourg (LU)

(73) Assignee: EPYGON, Paris (FR)

( * ) Notice: Subject to any disclaimer, the term of this patent is extended or adjusted under 35 U.S.C. 154(b) by 91 days.

(21) Appl. No.: 16/487,099

(22) PCT Filed: Jan. 19, 2018

(86) PCT No.: PCT/EP2018/051361
§ 371 (c)(1),
(2) Date: Aug. 20, 2019

(87) PCT Pub. No.: WO2018/149587
PCT Pub. Date: Aug. 23, 2018

(65) Prior Publication Data
US 2021/0085452 A1  Mar. 25, 2021

(30) Foreign Application Priority Data

Feb. 20, 2017 (WO) .................. PCT/IB2017/050960

(51) Int. Cl.
*A61F 2/24* (2006.01)
(52) U.S. Cl.
CPC .... *A61F 2/2412* (2013.01); *A61F 2220/0075* (2013.01); *A61F 2250/0036* (2013.01)

(58) Field of Classification Search
CPC ............ A61F 2/2412; A61F 2250/0036; A61F 2220/0075
See application file for complete search history.

(56) References Cited

U.S. PATENT DOCUMENTS

| | | | | |
|---|---|---|---|---|
| 2009/0281618 A1* | 11/2009 | Hill | ........................ | A61F 2/2457 623/1.26 |
| 2011/0238167 A1* | 9/2011 | Dove | ..................... | B65B 55/18 623/2.13 |
| 2011/0295363 A1* | 12/2011 | Girard | ................... | A61F 2/2412 623/1.26 |
| 2014/0005771 A1* | 1/2014 | Braido | .................. | A61F 2/2418 623/2.12 |
| 2014/0005772 A1 | 1/2014 | Edelman et al. | | |
| 2015/0173599 A1 | 6/2015 | Brado et al. | | |

FOREIGN PATENT DOCUMENTS

DE  60124930 T2 *  9/2007  ........... A61F 2/2412

OTHER PUBLICATIONS

Hinton, Robert B., and Katherine E. Yutzey, "Heart valve structure and function in development and disease." Annual review of physiology 73 (2011): 29-46.
Search Report of PCT/EP2018/051361 dated Apr. 11, 2018.
Written Opinion of PCT/EP2018/051361 dated Apr. 11, 2018.

* cited by examiner

*Primary Examiner* — William H Matthews
(74) *Attorney, Agent, or Firm* — Finch & Maloney PLLC

(57) ABSTRACT

Prosthetic heart valve leaflet with a fixed end and a free end characterized by the fact that it has a variable thickness.

9 Claims, 3 Drawing Sheets

PROSTHETIC HEART VALVE LEAFLET WITH VARIABLE THICKNESS

CROSS REFERENCE TO RELATED APPLICATIONS

The present application is a United States national stage application of International patent application PCT/EP2018/051361 filed on Jan. 19, 2018 designating the United States, and claims foreign priority to International patent application PCT/IB2017/050960 filed on Feb. 20, 2017, the contents of both documents being herewith incorporated by reference in their entirety.

FIELD OF INVENTION

The present invention relates to prosthetic heart valves and more precisely to the leaflets that are used in such prostheses.

STATE OT THE ART

The heart has four valves located within the four chambers. They are critical to the proper flow of blood through the heart. All the valves, when functioning normally, act as one-way valves, allowing blood to flow either from one chamber to another, or allowing blood to flow out of the heart, in only one direction. The valves control the flow of blood through the heart by opening and closing during the contractions. Blood flows from low pressure atria to higher pressure ventricles, which in turn supply the great arteries. The left side of the heart maintains significantly higher pressures than the right side. As a result, the impact of various physiologic forces depends on the position and hemodynamic environment of the valve. There are three basic loading states that affect valve tissue during the cardiac cycle: flexure, shear and tension. Flexure occurs when the valve is actively opening or closing, shear occurs when blood is passing through the open valve, and tension occurs when the valve is closed.

Nature build cardiac valve to support the loading states over lifetime. The heart beats more than 100,000 times per day handling approximately 5 liters of blood per minute. Indeed, valve tissue has exceptionally high strain because the tissue cycles to a completely unloaded state with each heart-beat. These deformation forces result in a compensatory balance in cell matrix composition. For example, comparison of porcine aortic and pulmonary valves demonstrates that the left sided aortic valve is thicker predominantly as a result of increased collagen expression and increased thickness of the fibrosa layer (Hinton R B, Yutzey K E. Heart Valve Structure and Function in Development and Disease. Annu Rev Physiol. 2011; 73: 29-46). The distribution of extra cellular matrix components is critical to proper the valve function. To deal with the high pressure during closing, redundant tissue (increased thickness) is present at the tips of both atrioventricular and semilunar valves that provides functional valve closure or coaptation of the valve leaflets/cusps and ultimately competence when the valve is closed. There has to be a precise balance between stiffness and flexibility. Elastic fibers extend from the valve hinge to the closing or coapting edge and therefore do not run the entire length of a valve. The atrialis/ventricularis layer facilitates valve tissue movement by allowing extension and recoil of the valve during the cardiac cycle.

Normal aortic valves have three soft and pliable cusps: When they close, the valve competence depends on the coaptation of the three cusps. At the middle level of each cusps, the coaptation depth is 8-10 mm. The free margin of each cusp shows a central nodule (increase of thickness) called corpus of Arantius from which the ridges extend to the commissures. Each ridge forms the lower margin of coaptation surface of the valve. The closure is smooth and synchronous which prevents leaflet fatigue and optimize valve mechanics.

The mitral valve is composed of two leaflets, the anterior (or aortic) and posterior leaflets. The supporting tendinous cords (chordae tendineae) on the ventricular aspect of the valve leaflets are inserted into two well-defined papillary muscles that are continuous with the left ventricular myocardium. The posterior leaflet dominates the majority of the mitral valve annulus circumference, but the anterior leaflet is larger and makes up a greater area. They are flake-like structures derived from the endocardial protrusion and are composed of connective tissue covered with endocardium and inserted on the fibrous ring of the cardiac skeleton. The leaflets consist of basal, marginal and middle parts, although they are not completely divided but are as membranous tissue in a continuum with variable widths. Both leaflets present two zones from their base (annulus insertion) to the free margin (edge of the leaflet), the atrial zone smooth translucent and the coaptation zone thicker and rough due to the numerous chordae attachment. This area has a rugged appearance and is rightly called the pars rugose. The pars rugose is wider than the central zone of the leaflet and gradually reduces as it approaches the commissures. Between the pars rugose and its insertion into the annulus, the anterior leaflet has a vast area called the pars liscia, which corresponds to a zone on whose ventricular surface there are no chordae insertion. The reasons why the heart valves have different thickness from the annular insertion region up to the free edge (coaptation zone) are obvious. The thicker distal end increases the coaptation length at the edge of the leaflet/cusp to prevent regurgitation and the thinner middle portion to facilitate valve tissue movements or flexure (opening and closing) during the cardiac cycles. Based on the abovementioned histological/anatomical structure of the cardiac valves, the objective of this invention is to manufacture a cardiac bioprosthesis based on the same features of the native cardiac valves.

DESCRIPTION OF THE INVENTION

The invention consists of a prosthetic heart valve leaflet (biologic or synthetic) prosthesis where the thickness of the tissue is not the same all over the leaflet, as defined in the claims. In a preferred embodiment, the leaflet edge at the level of the attachment to the stent structure and/or at the coaptation zone the tissue is thicker than in the central leaflet zone. The advantage compared to standard prosthesis is mainly in terms of durability and hemodynamics because it reinforces the tissue at the coaptation zone where the stress is greater, as well as promoting an increasing in the coaptation area with the aim to reduce the risk of intra-prosthetic regurgitation keeping a better flexure of the leaflet. The invention may be advantageously used with transcatheter prostheses. Such prostheses are designed to be collapsed and introduced into a catheter. Thicker is the tissue inside the stent frame, less collapsible is the prosthesis and larger the delivery system must be, thus more difficult is the procedure. Currently, to increase resistance and long-term durability, it is necessary to use a thicker biological tissue (i.e. bovine pericardium more than 0.4 mm thickness), especially in the setting of mitral and aortic prosthesis where the pressure is very high or when large sizes are manufactured (larger is the diameter of the prosthesis, greater is the tension produced). However, this implies in a loss of the hemodynamic profile, the primordial functional characteristic of a cardiac prosthesis. Thanks to the present invention, a cardiac prosthesic (i.e. aortic, mitral, tricuspid or pulmonary) can be manufactured with a smaller leaflet thickness in its central part (thus providing a better flexure) without compromising durability or good coaptation and ultimately providing the right balance between stiffness and flexibility The invention will be better understood hereafter with examples illustrated by the following figures:

Figure 3:
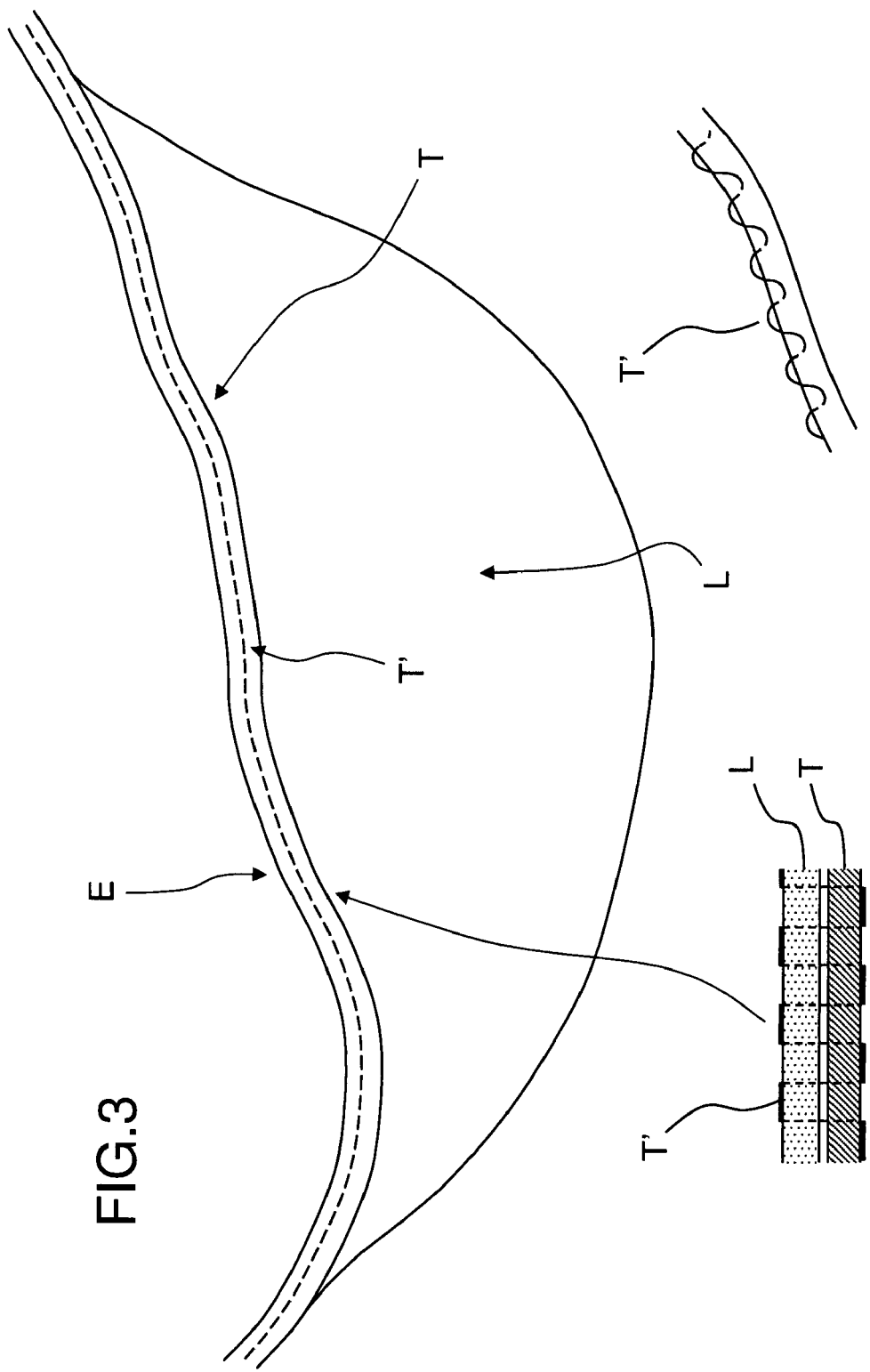

FIG. 3 discloses a second example of a leaflet with a variable thickness.

Figure 1:
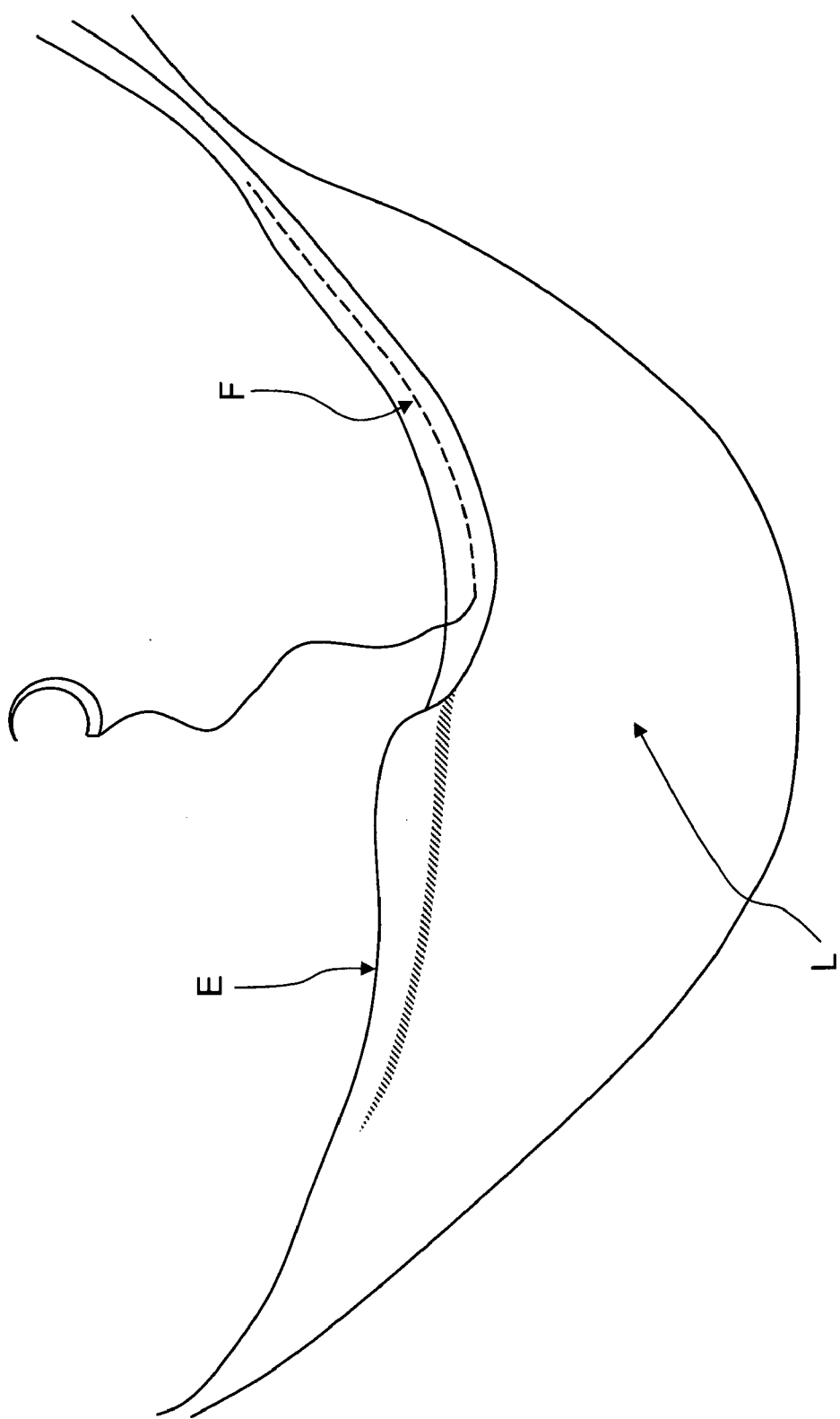
FIG. 1 shows a first example of a leaflet with a variable thickness (F=folded zone, E=leaflet edge, L=leaflet).
Figure 2:
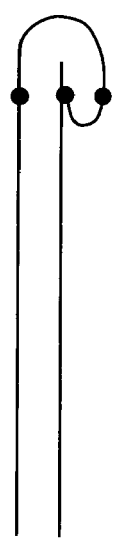
FIG. 2 shows a lateral view of the leaflet of FIG. 1.

One way of reinforcing the extremity of a tissue (see FIGS. 1 an 2) is to increase the thickness at the distal portion of the prosthetic leaflet, either at the level of the tissue/metal frame (stent) attachment or at the coaptation's free edge, is to produce a folding at the periphery of the tissue which will be used as leaflet. This can be done through a suture thereby doubling the thickness of the tissue. As abovementioned, in nature the coaptation depth is 8-10 mm, the length (or coaptation depth of the leaflet) may be modulated depending on the area of coaptation one wish to obtain i.e. 2-3-4-5 mm etc. Basically, if a comparison can be done, it's similar to sew a hem, taking the hem up or down depending how much one want the length of the coaptation zone (or attachment to the stent).

Figure 3B:
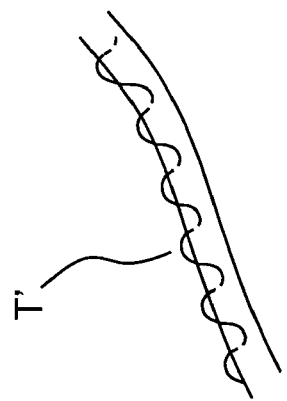

Another method for reinforcing the periphery of a tissue used in the manufacturing of a heart valve prosthesis (see FIGS. 3, 3a and 3b) is to perform a suture or attach a strip of tissue to strengthen the edges of the leaflet. This can be achieved by just placing a linear or running suture (preferably an ePTFE) all along the edge of the tissue or attaching a strip of material (ePTFE, polyester or other polymers' fabric, biologic tissue patches) at the edge of the leaflet.

Figure 3A:
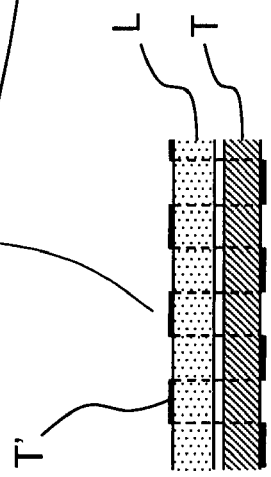

A strip of tissue T is sutured/attached to the edge of the leaflet to increase thickness at the coaptation zone. The reinforced edge may extend beyond the commissure to give greater strength during the tensioning phase. In FIG. 3a the leaflet L with the added strip of tissue T is represented in section. The leaflet L and the strip of tissue T are strictly joined together by linear stitches T'. The FIG. 3b an alternative way to stitch the leaflet L to the strip of tissue T by means of a running suture on the free edge T' is represented.

The invention is of course not limited to the above solutions. Any suitable way for obtaining a prosthetic heart valve with a variable thickness (for instance at the point of insertion between the leaflet and the stent or at the coaptation area) is also forming part of the invention. Any prosthetic heart valves with at least one leaflet is part of the invention.

The invention claimed is:

1. A prosthetic heart valve collapsible for introduction into a catheter, the prosthetic heart valve comprising:
    a frame, and
    a valve leaflet, the valve leaflet having
        a curved fixed end that is attached with respect to the frame, and
        a free end including a coaptation edge and a commissure,
        wherein at least a part of an edge of the leaflet, at the free end, is thicker than a remainder of the valve leaflet extending to and including the curved fixed end, and the thicker part of the edge of the leaflet is configured to extend beyond a commissure, such that the thickness of the edge of the leaflet at the level of a frame attachment is increased.

2. The prosthetic heart valve according to claim 1 wherein the thicker part of the edge of the leaflet is formed by a folding of the leaflet.

3. The prosthetic heart valve according to claim 1 wherein the thicker part of the edge of the leaflet is formed by a suture of a strip of material.

4. The prosthetic heart valve according to claim 1, wherein the thicker part of the edge of the leaflet is formed by a sutured biologic tissue patch.

5. The prosthetic heart valve according to claim 1, wherein the thicker part of the edge of the leaflet is formed by a sutured strip of material selected from: ePTFE, polymer fabric, polyester fabric.

6. The prosthetic heart valve according to claim 1, wherein the valve is a prosthetic mitral valve.

7. The prosthetic heart valve according to claim 1, wherein the valve comprises one leaflet.

8. The prosthetic heart valve according to claim 1, wherein the valve comprises plural leaflets.

9. A prosthetic heart valve collapsible for introduction into a catheter, the prosthetic heart valve comprising:
    a frame, and
    a valve leaflet, and the valve leaflet having
        a curved fixed end that is attached with respect to the frame, and
        a free end including a coaptation edge and a commissure,
        wherein at least a part of an edge of the leaflet, at the free end, is thicker than a remainder of the valve leaflet extending to and including the curved fixed end for increasing a coaptation length at the edge of the leaflet and preventing regurgitation while a middle portion of the leaflet is thinner to facilitate flexure during cardiac cycles, and the thicker part of the edge of the leaflet extends beyond a commissure.

* * * * *